United States Patent [19]
Parrent, Jr. et al.

[11] Patent Number: 4,920,060
[45] Date of Patent: Apr. 24, 1990

[54] DEVICE AND PROCESS FOR MIXING A SAMPLE AND A DILUENT

[75] Inventors: George B. Parrent, Jr., Chelmsford, Mass.; Harold Hauer, Wilmington, Del.

[73] Assignee: Hercules Incorporated, Wilmington, Del.

[21] Appl. No.: 180,729

[22] Filed: Apr. 8, 1988

Related U.S. Application Data

[63] Continuation of Ser. No. 918,704, Oct. 14, 1986, abandoned.

[51] Int. Cl.$^5$ .............................................. G01N 37/00
[52] U.S. Cl. .................... 436/178; 73/611 C; 422/70; 422/89; 422/82.09; 436/161; 436/179; 436/180
[58] Field of Search ................ 436/53, 57, 161, 178, 436/179, 142, 681; 422/79, 89; 73/61.1 R, 61.1 C

[56] References Cited

U.S. PATENT DOCUMENTS

| | | |
|---|---|---|
| 2,950,396 | 8/1960 | Schneider, Jr. . |
| 3,047,367 | 7/1962 | Kessler . |
| 3,098,717 | 7/1963 | Ferrari, Jr. . |
| 3,211,645 | 10/1965 | Ferrari ............................. 436/178 |
| 3,241,923 | 3/1966 | Ferrari . |
| 3,400,575 | 9/1968 | Madden ............................. 73/61 R |
| 3,522,819 | 8/1970 | Roberts . |
| 3,545,931 | 12/1970 | McKinley, Jr. ..................... 422/89 |
| 3,598,532 | 8/1971 | Adams et al. . |
| 3,718,434 | 2/1973 | Pierce ............................. 436/178 |
| 3,833,016 | 9/1974 | Lucero et al. . |
| 3,926,561 | 12/1975 | Lucero ............................. 436/178 |
| 3,991,055 | 11/1976 | Godin et al. . |
| 4,022,575 | 5/1977 | Hansen et al. . |
| 4,066,359 | 1/1978 | Bucalo ............................. 73/61 R |
| 4,108,602 | 8/1978 | Hanson et al. . |
| 4,617,032 | 10/1986 | Wells ............................. 436/161 |

FOREIGN PATENT DOCUMENTS

| | | |
|---|---|---|
| WO81/00911 | 4/1981 | PCT Int'l Appl. . |
| WO82/03690 | 10/1982 | PCT Int'l Appl. . |

*Primary Examiner*—Michael S. Marcus
*Attorney, Agent, or Firm*—Connolly & Hutz

[57] ABSTRACT

In a chemical analysis system a sample liquid is passed through a non-wetting porous membrane from a reservoir of sample liquid to a flowing stream of diluent which is constantly flowing when the sample liquid penetrates the membrane under positive pressure differential from the sample side of the membrane. The pressure differential is suitably obtained both by means for exerting pressure on the sample liquids as for example on a stream of sample liquid on the entry side of the membrane as well as a reduction in pressure on the exit side of the membrane. The passage of the sample liquid through the non-wetting porous membrane requires a minimum liquid entry pressure differential across the membrane to cause enough penetration to give a sample liquid which provides in an analyzed diluent stream a detectable presence of the sample liquid in an analytical detector receiving and measuring the stream.

11 Claims, 3 Drawing Sheets

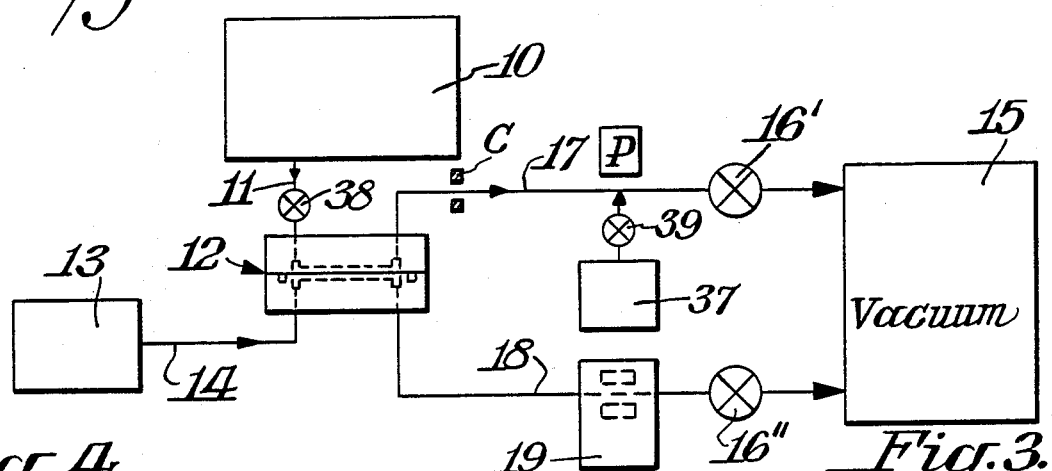
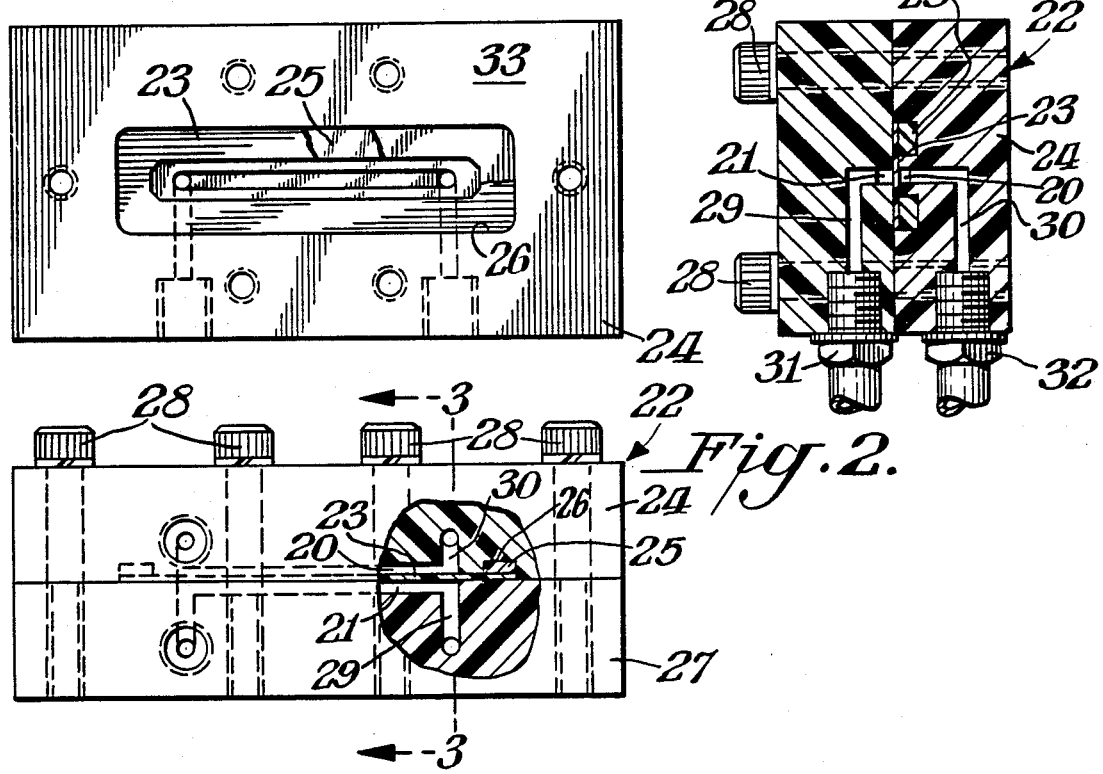
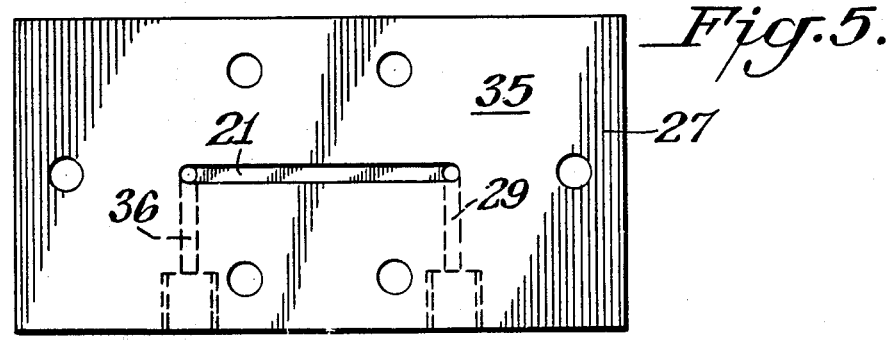

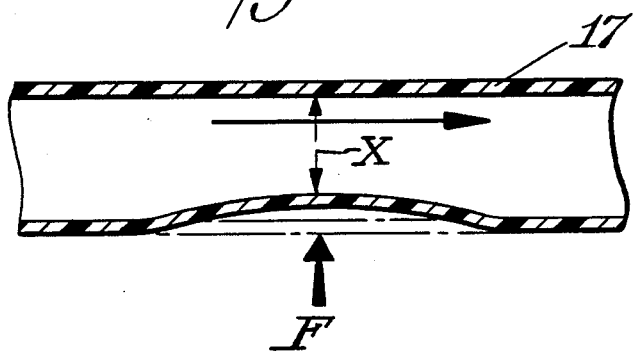
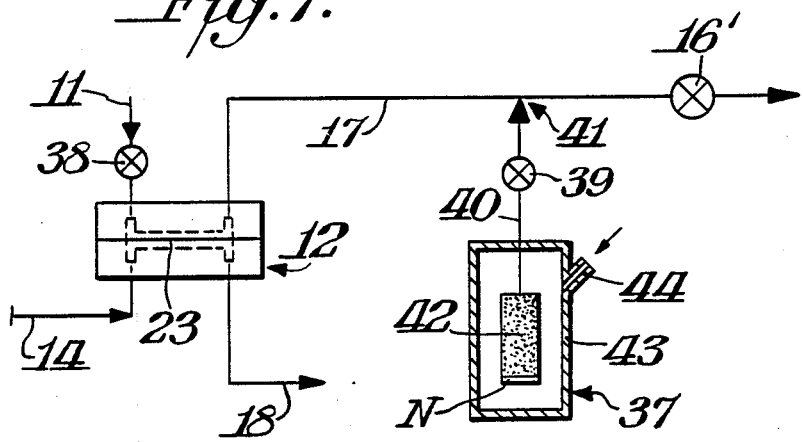
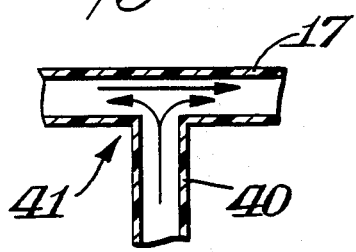

DEVICE AND PROCESS FOR MIXING A SAMPLE AND A DILUENT

This application is a continuation of application Ser. No. 06/918,704 filed Oct. 14, 1986, now abandoned.

REFERENCE TO CO-PENDING APPLICATION

This application discloses apparatus and method disclosed and claimed in co-pending Ser. No. 865,889 filed May 21, 1986 now abandoned for "Analyzing Apparatus and Method for Analysis of Liquid Samples", incorporated herein by reference.

This invention relates to dilution in the analysis of a liquid and more particularly the means and method of controlling the dilution of the liquid to be analyzed.

BACKGROUND OF THE INVENTION

Small volumes of liquid samples are analyzed in a detector which senses characteristics of the liquid sample and records the information. The sample liquid is selectively introduced into the detector and individually analyzed by sensing and measuring and the information is rapidly recorded.

In processing the liquid sample through the detector the sample liquid is diluted in a diluting liquid and the processing of the sample liquid and its analysis takes place with the sample liquid carried in a diluent.

The amount of dilution of the sample liquid in the diluent is controlled. Among other reasons for exercise of the control of the sample liquid is its conservation or that of the reagent. This is particularly important in an instance when the available volume of sample liquid is limited.

BRIEF DESCRIPTION OF THE INVENTION

In many automated chemical analysis systems the sample to be analyzed must be diluted, mixed with reagents, and passed on to a suitable sensor. The objects of this invention relate to the control, automation and fine tuning of the dilution process of such systems.

Among other objects of the present invention is a fine degree of control of the amount or percentage of dilution of the sample liquid in a diluent.

Another object of the invention is attaining a high percentage of dilution of the sample liquid in the diluent. A still further object of the invention is the provision of an effective dilution apparatus of simple construction which is easy to manufacture and use.

In general, in operation the sample liquid is passed through a non-wetting porous membrane from a reservoir of sample liquid to a flowing stream of diluent which is constantly flowing when the sample liquid penetrates the membrane under positive pressure differential from the sample side of the membrane. The pressure differential is suitably obtained both by means for exerting pressure on the sample liquids as for example on a stream of sample liquid on the entry side of the membrane as well as a reduction in pressure on the exit side of the membrane.

The passage of the sample liquid through the non-wetting porous membrane requires a minimum liquid entry pressure differential, hereinafter referred to as MLEPD, across the membrane to cause penetration through the pores and not the material. This MLEPD must be enough to give a penetration of sample liquid which provides in the analyzed diluent stream a detectable presence of the sample liquid in an analytical detector receiving and measuring the stream.

The invention will become more apparent upon consideration of the following detailed description taken together with the drawings.

DESCRIPTION OF THE DRAWINGS

FIG. 1 is a block diagram illustrating the apparatus and system embodying the present invention;

FIG. 2 is a side elevation partly broken away of the diluter assembly of this invention;

FIG. 3 is a sectional view of the diluter as illustrated in FIG. 2 taken on line 3—3 of FIG. 2 and rotated 90° counter clockwise;

FIG. 4 is a bottom plan view of the top plate of the diluter;

FIG. 5 is a top plan view of the bottom plate of the diluter;

FIG. 6 is a sectional view of a portion of the tubing conveying the stream of liquid sample;

FIG. 7 is a schematic diagram for explaining the functions of a means for controlling the pressure of the sample liquid on the membrane;

FIG. 8 is a sectional view of a T-joint in the tubing for conveying the sample liquid;

Detailed Description of the Invention

Figure 9:
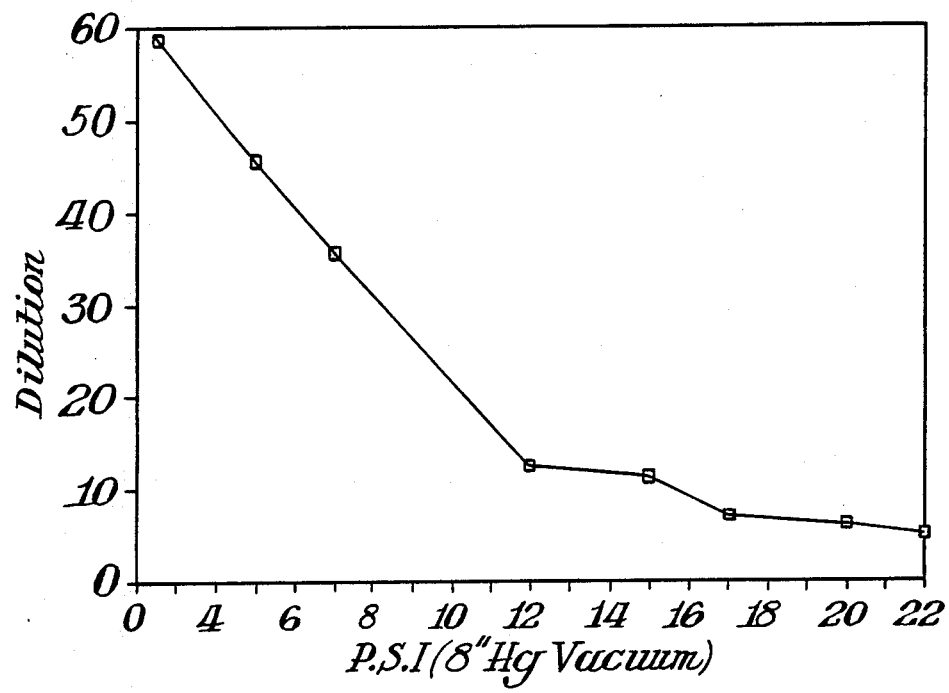
FIG. 9 is a graph diagrammatically illustrating the operation of the present invention in an apparatus with a specific sample liquid and membrane.

It will be understood that sample liquid as referred to herein refers to samples and reagents and other inputs as disclosed in Ser. No. 865,889 filed May 21, 1986, as identified above.

Reservoir as used herein refers to a part of the apparatus in which a sample liquid is held. In the illustrated embodiment the reservoir is that part of this apparatus which is positioned between valves 38 and valve 16' and includes a portion of conduit 11, the chamber 20 in diluter 12, port 30 and that portion of line 17 which connects port 30 with valve 16'.

In the apparatus of this invention samples and reagents are processed to form a stream of sample liquid which flows through the system to a detector which senses and determines properties in composition of the sample liquid. In FIG. 1, samples and reagents are provided to a supply means 10 to form a flowing liquid stream. The structure designated by the numeral 12 is a diluter. The diluter 12 is positioned to receive the flowing stream of sample liquid and a diluent stream transported from a diluent supply 13 through a line 14. In the diluter 12 a portion of the sample liquid is combined with the diluent to form a diluted liquid sample, which is transported from the diluter 12 through a line 18. The remainder of the sample liquid not transported to the diluent is expelled through line 17. The flowing streams are transported through the system by a driving force supplied either by a vacuum 15 or by a positive pressure force. The vacuum is connected to the end of the system through vacuum valves 16' and 16". A positive pressure source would be similarly connected through valves but in such a way as to push the sample. The valves are open to drive the liquid stream through the system. A representative system is disclosed in copending application Ser. No. 865,889 by David Davidson et al and particularly reference may be had to FIGS. 5A, 5B and pages 12-16 in this copending application and incorporated herein.

In FIG. 1 the sample liquid in the sample stream moves from the supply 10 into the diluter 12 through line 11 and controlled portion is forced from a reservoir formed in the diluter 12 and line 17 into the diluent as described below. On being withdrawn from the diluter 12 through line 18, the diluted liquid sample is passed through a detector device, such as photometric detector 19. The transport of the liquid streams through lines 11, 17 and 18 and diluter 12 is controlled by valve 16' in line 17 and valve 16" in line 18. In a normal operational sequence of the system of FIG. 1 the driving pressure difference may be in the range of 2½ to 15 inches of mercury. The valves 16' and 16" are suitable valves.

The structure of the diluter 12 is illustrated in FIGS. 2, 3, 4 and 5 and contains two small chambers 20 and 21 in a housing 22, which chambers 20 and 21 are separated by a laterally extending membrane 23. A suitable membrane 23 is a "Gore-Tex ® membrane" with a 1.0 micron pore size supported on a non-woven polypropylene sheet.

Referring to FIG. 2 the diluter 12 is shown in front elevation with the housing 22 partly broken away. The housing 22 has a top plate 24 in which is seated a sealing ring 25 in a groove 26 formed in the top plate 24. The housing 22 has a bottom plate 27 joined to and abutting the top plate 24. Chamber 20 is formed in top plate 24 and chamber 21 is formed in bottom plate 27 and the chambers 20 and 21 meet when the plates 24 and 27 are joined together.

FIG. 4 is a bottom plan view of the top plate 24 separated from the assembly in the housing 22. This plan view shows a planar surface 33 forming the face of plate 24 which interfaces with the bottom plate 27. The membrane 23 extending across the surface 33 is partly broken away to reveal the sealing ring 25. The sealing ring 25 in turn is partly broken away to illustrate its positioning in the groove 26. Ports 30 and 46 are shown in broken lines.

At the right side of FIG. 2 in the broken away area the chamber 20 and an end of the port 30 opening into the chamber 20 can be seen in full lines. To the left the remainder of the chamber is shown in broken lines thus illustrating the narrow elongated shape of the chamber 20.

FIG. 5 is a top plan view of the bottom plate 27 separated from assembly in the housing 22. This plan view shows a planar surface 35 forming the face of plate 27 which interfaces with the top plate 24. The narrow, elongated chamber 21 is shown and the ends of the port 29 and port 36 opening into the chamber 21 are shown.

The membrane 23 and the sealing ring 25 are positioned between the joined plates 24 and 27. The membrane 23 extends laterally between the chambers 20 and 21 so as to separate the chambers 20 and 21 from each other while providing with its porosity, passage for a liquid from the chamber 20 to chamber 21. The broken away section of plates 24 and 27 shown at the right of center in FIG. 2 illustrates the interface between the joined plates 24 and 27 at the right end of chambers 20 and 21. An edge of the membrane 23 extending under the sealing ring 25 is clamped beneath the sealing ring between the plates 24 and 27. The clamping action serves to both secure the membrane 23 in position between chambers 20 and 21 and to provide a fluid tight seal against seepage of the liquids. The plates 24 and 27 are tightly clamped together by bolts 28.

FIG. 3 is a section taken from the right side of FIG. 2 on line 3-3 across FIG. 2. In FIG. 3 the diluter 12 is turned at right angles to the orientation in FIG. 2. The bottom plate 27 is on the left side and the top plate 24 is on the right side in the housing 22 as illustrated in FIG. 3.

The chambers 20 and 21 at the center of the housing 22 are shown separated by the membrane 23 which is shown in cross-section. A port 29 provides a passageway to the chamber 21 in the bottom plate 27 while a port 30 provides a passageway to the chamber 20. Nipples 31 and 32 screwed into threaded recesses of the plates 27 and 24 respectively connect lines 18 and 17 to the ports 29 and 30 respectively. Thus, FIG. 3 illustrates the means for egress of the fluid stream from the diluter 12.

According to this invention the membrane 23 is distinguished by a non-wetting characteristic with respect to the sample liquid and the diluent. This non-wetting characteristic is a factor in the passage of the sample liquid through the membrane. Another factor is the force or pressure exerted on the sample liquid at the sample side of the membrane 23.

A non-wetting porous membrane is used to separate the process stream of sample liquid from a diluent stream. Since the membrane is not wet by the process stream liquid or the diluent, the normal forces of capillary action which would draw liquid across membrane, in either direction, are not operative. Thus liquid must be forced across the membrane by an external means such as an applied pressure differential. (This applied pressure differential may be created by a positive pressure source for example, reservoir or pump, or by a suitably configured and applied vacuum system.) In this application, the sample stream is forced through the membrane into the flowing diluent stream by the application of positive pressure in excess of MLEPD on the sample reservoir. The rate of transport into the diluent is a function of the membrane porosity, the wetting characteristics of the membrane as expressed by the MLEPD, the exposed surface area of the membrane, the pressure applied to the liquid to drive it across the membrane, and the pressure gradient in the diluent stream.

The total resistance to flow in any fluid path is an important component of the liquid transport. Thus, the resistance to flow across the membrane is dictated by the pore size and distribution within the membrane, the wettability of the membrane and any resistance to flow experienced by the liquid on its path to the membrane. For instance, a restriction in the tube through which the liquid passes will contribute to this resistance.

The pressure is applied to the sample liquid, according to the present embodiment, through the line 17. A source of pressure is represented in FIG. 1 by the block 37. To apply the pressure on the sample liquid, the valve 16' is closed and valve 38 in line 11 at the sample supply 10 is closed; it is possible to provide a differential pressure across the membrane 23 shown in FIG. 2 because the diluent is flowing in a stream from the supply 13, therefore, providing an open unrestricted path below the membrane. In the operation of this invention the diluent must be flowing through the chamber 21 from the supply 13 to effect the passage of the sample fluid through membrane 23. Moreover, the rate of transport across the membrane is effected by the flow rate of the diluent. Thus flowing of the diluent through the chamber 21 is a factor in the dilution achieved by the present invention.

When the valves 16' and 38 are closed the reservoir is formed and a positive pressure can be exerted from a source 37 after opening valve 39. This pressure pushes against the stream of the sample liquids in line 17 and in the chamber 20.

As pointed out above, according to this invention the relationship between the sample liquid and the non-wetting membrane is such that no transport of the liquid through the membrane is possible without the application of at least the MLEPD on the sample side of the membrane. When the applied pressure equals or exceeds the MLEPD, flow across the membrane results. The amount of dilution is a function of the applied pressure. This functional relationship is employed herein to provide a control of the percent of dilution of the sample. It is possible to accurately control high percentages of dilution.

In some constructions of the apparatus of this invention, the flow of the diluent stream across the membrane to a chamber, such as chamber 21, may draw minute amounts of sample liquid through the membrane, such as membrane 23, in the absence of a minimum liquid entry pressure on the sample side of the membrane. However, such transport is not accurately controllable and accordingly such phenomenon should it occur is not capable of contributing to the advantages of the present invention as outlined in the statement of objects above.

It is a feature of the present invention that when pressure is applied at P on the stream, the control of the transport of the sample liquid from the reservoir penetrating through the non-wetting membrane 23 is augmented to an appreciable degree. Thus, the amount of pressure influences the quantity of flow through the membrane. Thus variation in the exerted pressure is functionally related to the quantity of sample transported across the membrane 23 from the reservoir and delivered to the diluent chamber 21, as seen in FIG. 2. The amount of sample provided into a volume of diluent in a period of time is thus a function primarily of the characteristics of the membrane with respect to wetting and a variable applied pressure. That is, MLEPD defines the minimum working pressure on the reservoir on the sample side of membrane 23, i.e. at chamber 20, which provides a transport to the diluent stream to provide in the diluent stream of an amount of the sample which is measurably detectable in the analytical detector 19.

Further, it will be seen that at pressures above the MLEPD as determined by the characteristics of the material of a membrane 23, variations in pressure at P will influence the amount of transported sample by changing the rate of transport. Clearly this combination of factors provides a means for controlling the amount of dilution of the sample in the diluent. However, the effectiveness of the combination depends on the non-wetting characteristic of the membrane which is an essential part of the combination. As pointed out above, the present invention requires a MLPED which is attributable to and derived from the non-wetting characteristic of a membrane material as related to a sample liquid.

Non-wetting as referred to here can be defined in terms of the MLPED for the membrane as determined by the pressure difference observed at which liquid penetration into the membrane material has commenced. This can be carried out by a modification of ASTM method D774-67 and the related TAPPI method T403os-76. Briefly stated in this technique, water and the tested membrane are introduced into a Mullin Burst tester apparatus and hydrostatic pressure on the water and the membrane is slowly increased. The pressure at which droplets appear on the outside of the test film is the minimum water entry pressure. Liquids other than water may be used as appropriate to the selection of the sample liquid to be diluted and the membrane to be used to control this dilution. This pressure can be considered to be the threshold of the operation according to this invention. As explained below in greater detail, the threshold or MLEPD is a property of the particular material of the membrane as influenced both by the material compositions and the pore size of the passages and porosity through the membrane material. The passage of the sample liquid occurs only through the pores of the material, not through the material itself. The membrane of this invention as illustrated by membrane 23 in the figures, is composed of a material having pores and porosity which with a sample liquid is a non-wetting membrane. As used herein this refers to a liquid not penetrating the membrane in the absence of application of the MLEPD. Accordingly, the membrane may be composed as such materials, as the Gore-Tex ® membrane described below in the specific example with water as the sample liquid or stainless steel with a suitable sample liquid.

The control of the mixture of the sample liquid in the diluent according to this invention, is related to the excess of the applied pressure beyond the MLEPD of the membrane material. Pressures ranging above the minimum produce the transport of the sample liquid through the pores of the membrane in increasing amounts which vary as the function of the increase in applied pressure in the sample liquid in the reservoir at the sample side or chamber 20 as shown in FIG. 2. This pressure can be varied and controlled at P on line 17 from source 37 as shown in FIG. 1. It will be readily apparent that the variations in the amount of sample liquid penetrating through the pores has a direct effect on the amount of dilution taking place on the chamber 21 side of the membrane 23.

Thus while the particular membrane, as for example in the specifically described embodiment with its specific properties defines a threshold or minimum water entry pressure differential for the intermixture on the diluent side of membrane 23 (chamber 21 of FIG. 2) control of the dilution is affected by the pressure on the sample liquid in the reservoir. The capability of varying this pressure, such as variations in FIG. 1 from source 37 provides a control of the dilution which is independent of the membrane characteristics, i.e., pore sizes and porosity. The importance of this control is explained below.

The control of the pressure on the chamber 20 side of the membrane 23 which provides the variations in pressure can be effected by several means. Representative means are illustrated in FIGS. 6, 7 and 8.

Variations in the pressure in line 17 can be provided as by the combination of the source of pressure 37 and an adjustable clamp as shown in FIG. 1. The clamp C pinches the line 17 to provide variability in the line 17. For example, this can be used in combination with the pressure on line 17 from the source 37. As pointed out above, any variable resistance to the flow experienced by the sample liquid on the chamber 20 side of membrane 23 may contribute to the control of the flow across the membrane 23. Exerting resistance to flow in the reservoir portion of line 17 varies the pressure differential which is applied at membrane 23. Consequently, the rate of liquid transport through the diluter membrane 23 may be affected by varying a restriction in the tubing through which the liquid passes as by resistance at C or at P from the source of pressure 37 or both. This mechanism allows one to fine tune the rate of transport through the membrane and, therefore, the extent of dilution.

FIG. 6 is a sectional view of a portion of line 17 at pressure point F. FIG. 6 provides a representation of another means of applying pressure as a modification of the embodiment illustrated in FIG. 1 at P. In this embodiment the line 17 has a flexible wall area at pressure point F and thus the tube can be flexed. Flexing the tube 17 inwardly at F forms a narrowed gut X in the interior passage. Flexing the tube 17 outward increases the interior passage.

Another device for varying the pressure differential between the reservoir portion of line 17 and diluent side of the membrane by restriction of the flow is illustrated in FIGS. 7 and 8. An air line 40 joins the line 17 in a T-joint 41 and applies air under variable pressure into the line 17 perpendicularly across the axis of flow in line 17. A valve 39 is provided in air line 40. An enlargement of the T-joint 41 in section is shown in FIG. 8 illustrating the directions of air flow from the pressure source 37. The directional arrows show that the air flow is in both directions at the T-joint 41.

The air pressure in line 40 can be supplied and controlled by means of the embodiment of the source of pressure 37 as depicted in FIG. 7. A porous tube 42 in a sealed chamber 43 is attached to the line 40 which extends from the chamber 43 to the T-joint 41. Air (or other driving fluid) is pumped into the chamber under pressure through an inlet 44. The porous tube sealed at end N provides resistance to flow of the driving fluid. The key concept is that a membrane or porous tube serves as a resistance modifying the pressure differential source to a suitable working range.

An example of a specific application of the present invention in the dilution of a sample liquid is presented in the data set forth in FIG. 9. This data was obtained in a dilution apparatus as described herein having a Gore-Tex ® polytetrafluoroethylene membrane, with a pore size of 0.45 micron and typical porosity of 84% seated in the dilution chamber. The vacuum pressure in the analysis stream, line 18 in FIG. 1 was 8 inches of mercury. The abcissa indicates the positive pressure applied at point P when valves 16' and 38 (FIG. 1) are closed. The pressure is shown in pounds per square inch pressure on liquid in chamber 20, or the reservoir, and a vacuum on the diluent or analysis stream measured in 8 inches of mercury. This pressure gradient forces the sample through the membrane into the diluent stream 18. The ordinate of the graph expresses the dilution of the methyl orange sample in terms of the absorbance signal (520 nm) as the ratio as follows:

Dilution=(concentration in)/(concentration out).
The concentration dependence of the absorbance signal observed at the photodetector 19, FIG. 1 was established by passing known concentrations of methyl orange indicator solution directly through the photodetector.

Figure 10:
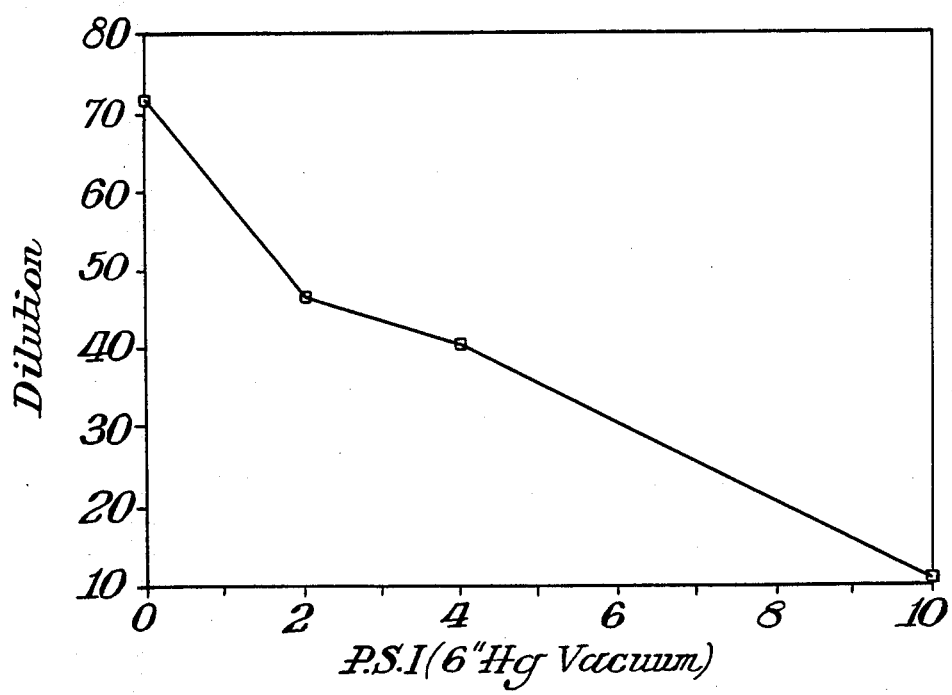
FIG. 10 is a graph diagrammatically illustrating the operation of the present invention in an apparatus with a specific sample liquid and another specific membrane.

A second example is presented in the data of FIG. 10. This data was obtained in the diluter apparatus as described herein have a Gore-Tex ® membrane of 1 micron pore size and of 91% typical porosity was used in the diluter. The system vacuum pressure was 6 inches or mercury for this experiment. Bromothymol blue indicator solution in 0.01M sodium hydroxide was used to calibrate the diluter and the photometer. The pressure shown on the abscissa is in pounds per square inch in liquid in chamber 20, or the reservoir, and a vacuum on the diluent or analysis stream of measured in 6 inches of mercury.

The manner in which the rate of the liquid transport, or penetration, through the membrane is affected by a constriction in line 17 along with the application of a positive pressure at P is now illustrated in the following example. A Gore-Tex membrane of 10-15 micron pore size and 98% typical porosity was folded over to provide a double thickness and inserted in the diluter 12. The apparatus was operated with sample liquid supplied from supply 10 and an applied vacuum as disclosed herein. Without any pressure on the tube 17 (FIG. 1) no control over the rate of transport of sample through the diluter membrane could be established. A laboratory C-clamp was applied at point C and tightened to a position which permitted the use of the positive pressure source to control the liquid transport across the membrane. For example, with pressure from source 37, the tighter the clamp C the more pressure required from source 37 to exert pressure on membrane 23. The extent of the transport and therefore dilution, was confirmed by measuring the displacement of liquid in tube 17 after 10 seconds as a function of positive pressure to the tube at point P. Table 1 summarizes the results.

TABLE 1

| System Vacuum | Positive Pressure | Liquid Displacement |
|---|---|---|
| 4.75" Hg | 0 psi | 2 mm |
| 5.75 | 5 | 153 |
| 6.5 | 5 | 162 |
| 6.5 | 5 | 165 |

As a specific example of a suitable membrane, reference is made to "GORE-TEX" (registered trademark) membranes in the range described in the "GORE-TEX" brochure as follows:

| GORE-TEX ® Membrane Properties | | |
|---|---|---|
| Pore Size (micron) | Typical Thickness | Minimum Water Entry Pressure PSI |
| 0.45 | 0.003" | 20 |
| 1.00 | 0.003" | 10 |

Gore-Tex ® membrane is an expanded, 100% virgin polytetrafluoroethylene membrane.

Other suitable membranes may be hydrophobically modified Nuclepore ® polycarbonate or polyester material for processing aqueous solutions, or non-modified polycarbonate or polyester Nuclepore ® material for use with other solutions.

It will be readily apparent that there are other membranes which can be provided in accordance with this invention so as to be impervious and not allow entrance or passage in controllably detectable amounts of suitable selected sample liquids to a diluent stream in the absence of a minimum liquid entry pressure differential.

While the invention has been particularly shown and described with reference to preferred embodiments thereof, it will be understood that those skilled in the art that changes in form and details may be made therein without departing from the spirit of the invention, the scope of which is defined in the appended claims.

What is claimed is:

1. A method of controlling dilution of a sample in a measurement of the characteristics of a sample liquid in an analytical detector,
   comprising the steps of
   providing a supply of sample liquid,
   providing a cavity having a non-wetting porous membrane and having a supply chamber on one side of said membrane and a dilution chamber on the other side of said membrane,
   and having a first conduit from the sample liquid to the supply chamber and from the supply chamber to a discharge,
   transporting the sample liquid through the first conduit to a first surface of said membrane at said supply chamber and from the supply chamber to the discharge,
   restricting the flow of said transported sample liquid through said first conduit and supply chamber by a plurality of valve means positioned between said sample supply and the supply chamber and the supply chamber and the discharge,
   controllably operating and adjusting said valve means to constrict the sample liquid to form a reservoir of sample liquid contained in the first conduit and supply chamber between said plurality of valve means,
   providing means at said reservoir for variably applying pressure on said contained sample liquid in said reservoir,
   controlling application of variable pressure on the sample liquid contained in the reservoir to vary and control the amounts of sample liquid transported through the membrane which is equal to or in excess of the minimum liquid entry pressure for the transport through the membrane,
   passing a stream of diluent through the dilution chamber across a second surface of the membrane and a second conduit to an analyzer for sensing the properties and composition of the sample liquid in the diluent,
   and said diluent stream drawing not more than minute amounts of sample through said membrane,
   and applying said pressure on said sample contained in said reservoir to produce a pressure differential between pressure on the sample liquid at the first surface of the membrane and the pressure in the flowing diluent stream across the other surface in excess of the maximum liquid entry pressure differential to pass sample liquid through the membrane so that the amount of dilution of the sample liquid in the diluent is a function of said applied pressure.

2. The method of claim 1 wherein said sample liquid is an aqueous solution and said minimum liquid entry pressure differential is the minimum water entry pressure differential sufficient to provide controllably detectable amounts of said aqueous solution in said diluent stream.

3. The method as claimed in claim 1 wherein the variable pressure which is equal to or in excess of the minimum liquid entry pressure is applied on said sample liquid and provides controlled quantities of said sample liquid in the diluent for analysis and
   the transport of the sample liquid through the membrane is insufficient for controllably measuring characteristics of the sample liquid in the absence of the application of at least said minimum liquid entry pressure differential on the sample liquid in the reservoir on the one surface of the membrane.

4. The method as claimed in claim 1, wherein the minimum liquid entry pressure differential is a positive pump generated force applied to said sample liquid.

5. A method as claimed in claim 1 in which a variable pressure which is equal to or in excess of the minimum liquid entry pressure is applied to the sample liquid in the reservoir by a second fluid located adjacent to the reservoir and the pressure differential is modified by a resistance to the flow of the second fluid.

6. Apparatus for controlling the dilution of a sample in a diluent in the analysis of the sample in a detector comprising the combination of a cavity having a non-wetting porous membrane separating said cavity into a supply chamber and a dilution chamber, a supply of a sample liquid, a first conduit for transporting the sample liquid from the supply to the supply chamber and from the supply chamber to a discharge means, a first valve positioned in said first conduit between the supply and the supply chamber actuable to close and hold sample liquid in said conduit and supply chamber, a second valve positioned in said first conduit between said supply chamber and said discharge actuatable to close and hold sample liquid in said conduit and supply chamber, a reservoir comprised of said first and second valves, said supply chamber and said first conduit, a means for selectively applying pressure on said sample liquid in said reservoir, including said first conduit and supply chamber, positioned between said second valve and said supply chamber, said pressure applying means having a control for varying the applied pressure, said first and second valves, pressure applying means and control being operative to initiate and cease the application of pressure on said transported sample liquid in said supply chamber in excess of the minimum liquid entry pressure differential a second conduit for transporting a diluent stream through said dilution chamber, which diluent stream transported through said dilution chamber draws not more than minute amounts of sample through the membrane in the absence of a minimum liquid entry pressure upon the sample in the supply chamber, an analyzer for sensing said sample in the diluent so constructed and arranged as to receive diluted sample from the dilution chamber, said membrane being impervious to the passage, in a controllable detectable amount, of said sample from the supply chamber to the dilution chamber in the absence of the application of pressure in the reservoir on the transported sample liquid in excess of the minimum liquid entry pressure differential said minimum liquid entry pressure differential being the differential across the membrane to provide sample penetration through the pores and no substantial sample penetration through the membrane material.

7. Control apparatus as claimed in claim 6 wherein said porous membrane is impermeable to passage of the sample liquid by capillary action.

8. The apparatus in claim 6 wherein said source of pressure is a flexible portion of said first conduit said flexible portion being compressible to vary the applied pressure on said sample liquid.

9. The apparatus as claimed in claim 6 wherein said membrane consists of Gore-Tex ® polytetrafluoroethylene membrane.

10. The apparatus as claimed in claim 9 wherein the membrane has a pore size in the range of 0.45 micron to 15 micron.

11. The apparatus as claimed in claim 6 wherein said membrane is selected from the group consisting of hydrophobically modified Nuclepore polycarbonate and polyester material.

* * * * *